(12) United States Patent
Xu

(10) Patent No.: US 10,138,224 B2
(45) Date of Patent: Nov. 27, 2018

(54) PREPARATION METHOD OF ROCILETINIB

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/952,202

(22) Filed: Apr. 12, 2018

(65) Prior Publication Data

US 2018/0230133 A1 Aug. 16, 2018

Related U.S. Application Data

(63) Continuation of application No. PCT/CN2016/098852, filed on Sep. 13, 2016.

(30) Foreign Application Priority Data

Oct. 26, 2015 (CN) .......................... 2015 1 0701079

(51) Int. Cl.
*C07D 239/48* (2006.01)
*C07D 403/12* (2006.01)

(52) U.S. Cl.
CPC ......... *C07D 403/12* (2013.01); *C07D 239/48* (2013.01)

(58) Field of Classification Search
CPC .................................................... C07D 239/48
See application file for complete search history.

(56) References Cited

FOREIGN PATENT DOCUMENTS

| | | |
|---|---|---|
| CN | 104860890 A | 8/2015 |
| CN | 105198821 A | 12/2015 |
| WO | 2012061299 A1 | 5/2012 |
| WO | 2012064706 A1 | 5/2012 |
| WO | 2015158310 A1 | 10/2015 |

*Primary Examiner* — Bruck Kifle
(74) *Attorney, Agent, or Firm* — Perkins Coie LLP

(57) ABSTRACT

Disclosed is a method for preparing Rociletinib. 2-[[4-(4-acetyl-1-piperazinyl)-2-methoxyphenyl]amino]-5 -(trifluoromethyl)-pyrimidin-4-one is obtained by means of a condensation reaction of easily obtainable raw materials 5-(trifluoromethyl)uracil and 4-(4-acetylpiperazin-1-yl)-2-methoxyaniline, an intermediate is subjected to a halogenation reaction and an amination reaction to produce Rociletinib (I). The preparation method has easily obtainable raw materials, a simple process, is economic and environmentally friendly, and is suitable for industrial production.

10 Claims, No Drawings

PREPARATION METHOD OF ROCILETINIB

CROSS REFERENCE TO RELATED APPLICATIONS

This application is a continuation of PCT/CN0216/098852 filed Sep. 13, 2016, which claims priority to CN 2015107010795 filed Oct. 26, 2015, both of which are incorporated herein by reference.

TECHNICAL FIELD

The present invention belongs to the technical fields of design of organic synthetic routes, and preparation of active pharmaceutical ingredients and intermediates thereof, and particularly relates to a preparation method of an experimental drug rociletinib for treating non-small cell lung cancer.

BACKGROUND ART

Rociletinib is an oral irreversible-mutation third-generation epidermal growth factor receptor (EGFR) inhibitor developed by Clovis Oncology. The drug can inhibit key activating mutation and T790M resistance mutation, leaving a wild-type EGFR signal inactive. On May 20, 2014, the FDA awarded Breakthrough Therapy Designation to this experimental drug, for the second-line treatment of EGFR-mutated non-small cell lung cancer (NSCLC) carrying T790M as a single-drug therapy. Since the drug does not have a standard Chinese translation, the applicant transliterated this as "luoxitini" by transliterating.

The chemical name of rociletinib (I) is: N-[3-[[2-[[4-(4-acetyl-1-piperazinyl)-2-methoxyphenyl]amino]-5-(trifluoromethyl)-4-pyrimidyl]amino]phenyl]-2-acrylamide, and the structural formula is:

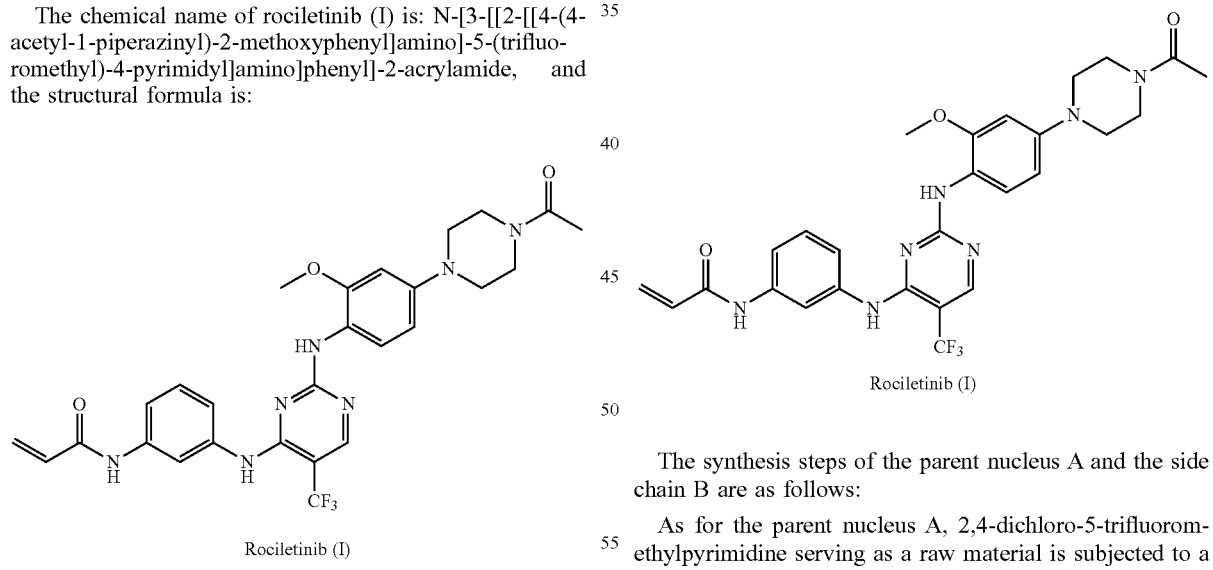

International patents WO2012061299, WO2013138502 and WO2014182593 reported on the synthesis of rociletinib. The core preparation steps include condensation reactions of a parent nucleus A and a side chain B. As for the sequence of Boc-protection and acryloylation reaction on the parent nucleus A and the order of N-protection and acetylation reaction on piperazine on the side chain B, corresponding changes can be made according to different reaction requirements, and have no significant impact on the overall reaction route.

The synthesis steps of the parent nucleus A and the side chain B are as follows:

As for the parent nucleus A, 2,4-dichloro-5-trifluoromethylpyrimidine serving as a raw material is subjected to a 4-chlorine substitution reaction with N-Boc-m-phenylenediamine to generate a parent nucleus intermediate A, the intermediate A can be directly subjected to a condensation reaction with the side chain B to generate a protected intermediate C, and the intermediate C is subjected to deprotection and acryloylation reaction to obtain the target compound rociletinib. The parent nucleus A can also be directly subjected to deprotection and acryloylation reaction to obtain another parent nucleus intermediate A', and the intermediate A' reacts with the side chain B to directly produce rociletinib.

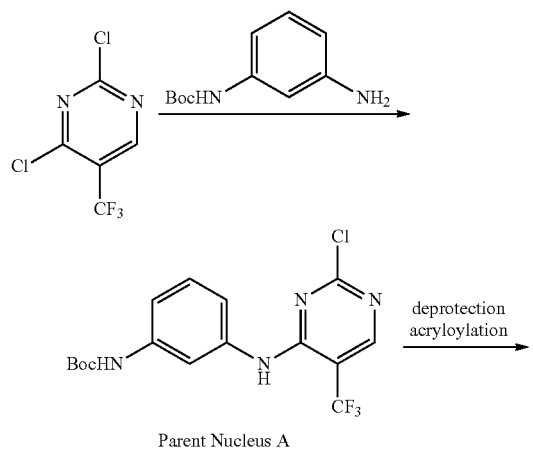

Parent Nucleus A

Parent Nucleus A'

The side chain B is prepared by performing a halogenation reaction and a nitro reduction reaction on a raw material N-acetylpiperazidine.

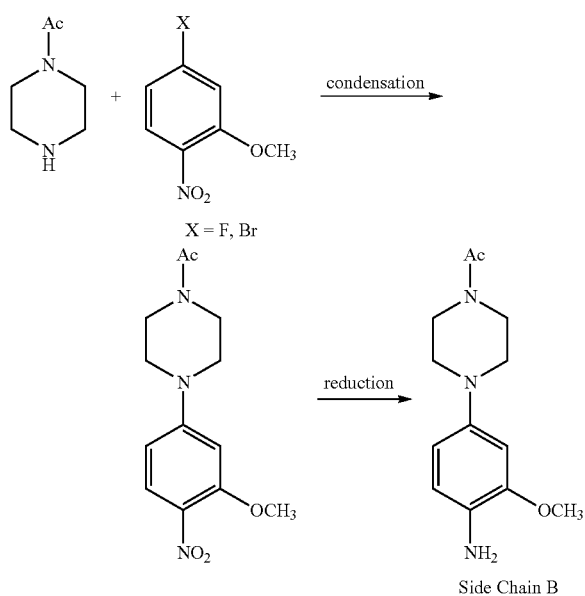

Side Chain B

By analyzing the above synthetic route, although the target compound rociletinib can be successfully prepared for the first time, there are still disadvantages such as unobtainable raw materials, too many steps, low yield of partial reactions and the like. Especially for the parent nucleus A, on the one hand, raw materials are difficult to obtain, and more importantly, the activities of two chlorine atoms on the pyrimidine ring are not much different, so that the selectivity of two substitution reactions of aromatic amines is poor, thereby having an adverse effect on the overall yield of the preparation and on the purification of the aftertreatment.

In view of the existing process defects, a preparation technology which is simple in process, economical, environment-friendly and superior in quality has been developed. In particular, the search for a process that can adapt to industrial production has important practical significance for improving the economic and social benefits of the drug.

SUMMARY OF THE INVENTION

The present invention aims to provide a preparation method of rociletinib (I), which has the advantages of easily obtainable raw materials and simple process, is economical and environment-friendly and is suitable for industrial production.

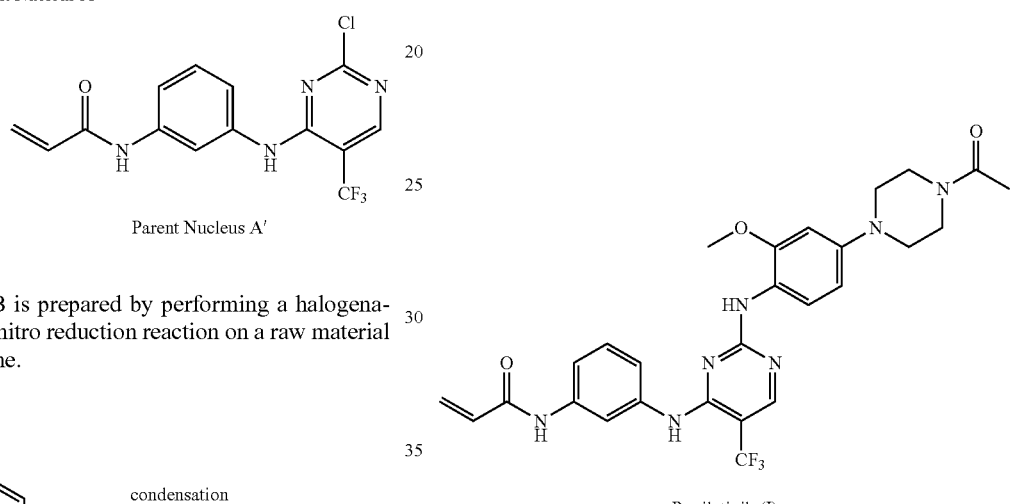

Rociletinib (I)

In order to achieve the above-mentioned goals, 5-(trifluoromethyl)uracil (II) and 4-(4-acetylpiperazin-1-yl)-2-methoxyaniline (III) are subjected to a condensation reaction under the actions of a condensing agent and an alkali accelerator to obtain 2-[[4-(4-acetyl-1-piperazinyl)-2-methoxyphenyl]amino]-5-(trifluoromethyl)-pyrimidin-4-one (IV), and the 2-[[4-(4-acetyl-1-piperazinyl)-2-methoxyphenyl]amino]-5-(trifluoromethyl)-pyrimidin-4-one (IV) and a halogenating agent are subjected to a halogenating reaction under the action of an acid-binding agent to obtain 2-[[4-(4-acetyl-1-piperazinyl)-2-methoxyphenyl]amino]-5-(trifluoromethyl)-4-halogeno-pyrimidine (V), and the 2-[[4-(4-acetyl-1-piperazinyl)-2-methoxyphenyl]amino]-5-(trifluoromethyl)-4-halogeno-pyrimidine (V) is subjected to an amination reaction under the action of a catalyst to obtain rociletinib (I).

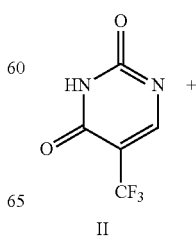

II

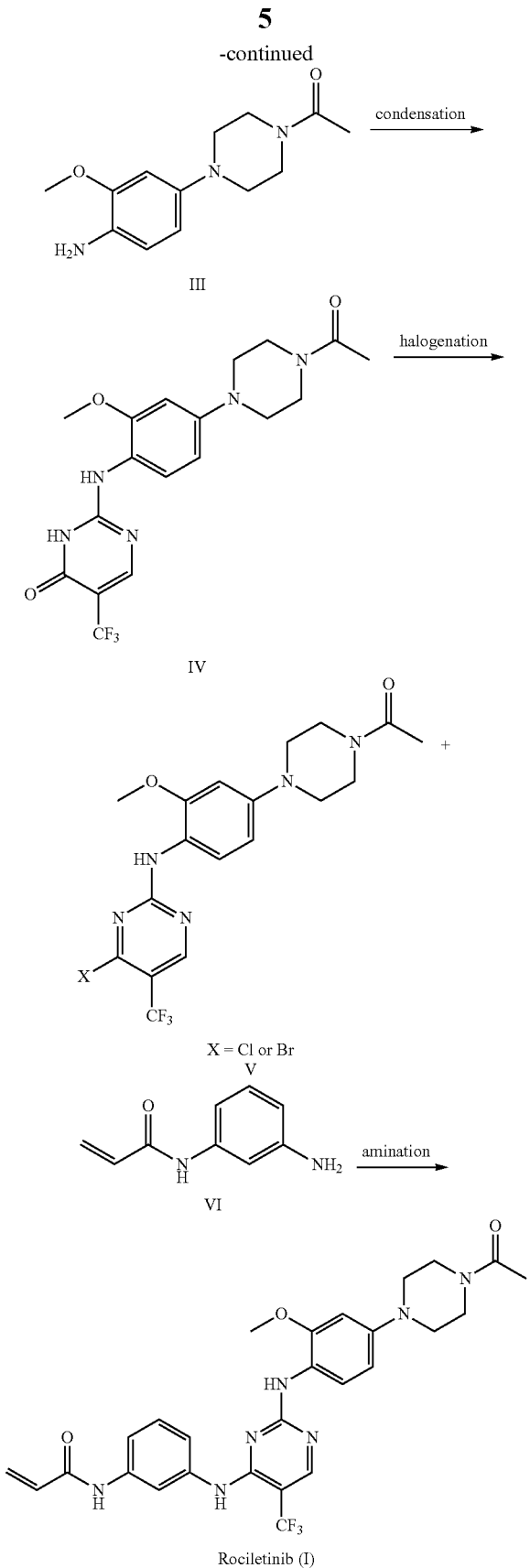

In addition, the present invention also provides the following appended technical scheme:

The mole ratio of 5-(trifluoromethyl)uracil (II) to 4-(4-acetylpiperazin-1-yl)-2-methoxyaniline (III) serving as condensation reaction raw materials is 1 to (0.5-1.5), preferably 1 to (0.9-1.1).

The condensing agent of the condensation reaction is N,N-dicyclohexylcarbodiimide, carbonyl diimidazole, N,N'-diisopropylcarbodiimide, 1-hydroxybenzotriazole, O-(benzotriazol-1-yl)-N,N,N',N'-tetramethyluronium tetrafluoroborate, O-(7-azabenzotriazol-1-yl)-N,N,N',N'-tetramethyluronium hexafluorophosphate, O-(benzotriazol-1-yl)-N,N,N',N'-tetramethyluronium hexafluorophosphate or (benzotriazol-1-yloxy)tris(dimethylamino)phosphonium hexafluorophosphate, preferably, O-(benzotriazol-1-yl)-N,N,N',N'-tetramethyluronium hexafluorophosphate or (benzotriazol-1-yloxy)tris(dimethylamino)phosphonium hexafluorophosphate.

The alkali accelerator of the condensation reaction is triethylamine, pyridine, 2,6-dimethylpyridine, 4-dimethylaminopyridine, N-methylmorpholine, N-ethylmorpholine, diisopropylethylamine, 1,5-diazabicyclo[4.3.0]non-5-ene, 1,8-diazabicyclo[5.4.0]undec-7-ene or 1,4-diazabicyclo[2.2.2]octane, preferably, 1,8-diazabicyclo[5.4.0]undec-7-ene, 1,5-diazabicyclo[4.3.0]non-5-ene or 1,4-diazabicyclo[2.2.2]octane.

A solvent of the condensation reaction is methylbenzene, dimethylbenzene, ethyl acetate, isopropyl acetate, butyl acetate, chloroform, dimethyl sulfoxide, N,N-dimethylformamide or acetonitrile, preferably acetonitrile.

The temperature of the condensation reaction is 0-120° C., preferably 50-80° C.

The halogenating agent of the halogenation reaction is oxalyl chloride, sulfuryl chloride, phosphorus trichloride, phosphorus pentachloride, thionyl chloride, phosphorus oxychloride or phosphorus tribromide, preferably phosphorus oxychloride or phosphorus tribromide.

The acid-binding agent of the halogenation reaction is triethylamine, pyridine, 2,6-dimethylpyridine, 4-dimethylaminopyrkline, N-methylmorpholine, N-ethylmorpholine or diisopropylethylamine, preferably pyridine, 2,6-dimethylpyridine or diisopropylethylamine.

The temperature of the halogenation reaction is 0-100° C., preferably 40-70° C.

The halogen in the halogenation reaction product 2-[[4-(4-acetyl-1-piperazinyl)-2-methoxyphenyl]amino]-5-(trifluoromethyl)-4-halogeno-pyrimidine is chlorine or bromine.

The halogenation reaction product can be directly subjected to the amination reaction without purification.

The catalyst of the amination reaction is potassium carbonate, lithium carbonate, cesium carbonate, potassium tert-butoxide, sodium tert-butoxide, sodium hydroxide, potassium hydroxide, sodium methoxide or sodium ethylate, preferably cesium carbonate or potassium tert-butoxide.

A solvent of the amination reaction is 1,2-dichloroethane, tetrahydrofuran, acetonitrile, dioxane, benzene, methylbenzene, dimethylbenzene, dimethyl sulfoxide or N,N-dimethylformamide, preferably dimethyl sulfoxide or N,N-dimethylformamide.

The temperature of the amination reaction is 25-150° C., preferably 90-110° C.

Compared with the prior art, the preparation method of rociletinib (I) of the present invention has the characteristics of easily obtainable raw materials and simple process, is economical and environment-friendly, and thus, is beneficial to industrial production of the active pharmaceutical ingredient, thereby promoting the development of economic technology of the active pharmaceutical ingredient.

DETAILED DESCRIPTION OF THE INVENTION

A nonrestrictive description of the technical schemes of the present invention will be given below in combination with several preferred embodiments. For preparation of the raw material 5-(trifluoromethyl)uracil (II), please refer to the preparation of the same compound in "Angewandte Chemie, International Edition, 53(44), 11868-11871; 2014" or "Journal of Fluorine Chemistry, 77(1), 93-95; 1996". For preparation of the raw material 4-(4-acetylpiperazin-1-yl)-2-methoxyaniline (III) and the raw material N-(3-aminophenyl)-2-acrylamide (VI), please refer to the preparation of the same compounds in world patents WO2012061299 and WO2015117547.

Embodiment 1

In a nitrogen atmosphere, adding 5-(trifluoromethyl)uracil (II) (1.80 g, 10 mmol), (benzotriazol-1-yloxy)tris(dimethylamino)phosphonium hexafluorophosphate (6.63 g, 15 mmol) and acetonitrile (50 mL) into a three-neck flask. With stirring, dropwisely adding 1,8-diazabicyclo[5.4.0]undec-7-ene (2.28 g, 15 mmol), and after finishing addition, reacting at room temperature for 12 hours. Heating to 60° C., and continuing the reaction for 12 hours. Performing reduced pressure distillation to remove the solvent, adding 100 mL of ethyl acetate for dissolving, and washing with 20 mL of 2M sodium hydroxide. Separating out an organic phase, drying and concentrating under reduced pressure. Dissolving the residue with 100 mL of tetrahydrofuran, adding 4-(4-acetylpiperazin-1-yl)-2-methoxyaniline (III) (2.49 g, 10 mmol) and sodium hydride (0.32 g, 13 mmol), heating to 70° C., stirring to react for 5 hours, and performing TLC monitoring until the reaction is finished. Quenching the reaction with saturated brine, extracting with ethyl acetate, separating out the organic phase, drying, performing reduced pressure distillation to recover the solvent, and recrystallizing the obtained residue with ethanol to obtain 3.37 g of a light yellow solid 2-[[4-(4-acetyl-1-piperazinyl)-2-methoxyphenyl]amino]-5-(trifluoromethyl)-pyrimidin-4-one (IV), wherein the yield is 82.0%; EI-MS m/z: 412 [M+H]$^+$.

Embodiment 2

In a nitrogen atmosphere, adding 5-(trifluoromethyl)uracil (II) (1.80 g, 10 mmol), O-benzotriazol-1-yl-tetramethyluronium hexafluorophosphate (5.69 g, 15 mmol) and acetonitrile (50 mL) into a three-neck flask. With stirring, dropwisely adding 1,5-diazabicyclo[4.3.0]non-5-ene (1.86 g, 15 mmol), and after finishing addition, reacting at room temperature for 12 hours. Heating to 60° C., and continuing the reaction for 12 hours. Performing reduced pressure distillation to remove the solvent, 100 mL of adding ethyl acetate for dissolving, and washing with 20 mL of 2M sodium hydroxide. Separating out an organic phase, drying and concentrating under reduced pressure. Dissolving the residue with 100 mL of tetrahydrofuran, adding 4-(4-acetylpiperazin-1-yl)-2-methoxyaniline (III) (2.49 g, 10 mmol) and sodium hydride (0.32 g, 13 mmol), heating to 70° C., stirring to react for 5 hours, and performing TLC monitoring until the reaction is finished. Quenching the reaction with saturated brine, extracting with ethyl acetate, separating out the organic phase, drying, performing reduced pressure distillation to recover the solvent, separating out the organic phase, drying, performing reduced pressure distillation to recover the solvent, and recrystallizing the obtained residue with ethanol to obtain 3.30 g of a light yellow solid 2-[[4-(4-acetyl-1-piperazinyl)-2-methoxyphenyl]amino]-5-(trifluoromethyl)-pyrimidin-4-one (IV), wherein the yield is 80.3%; EI-MS m/z: 412 [M+H]$^+$.

Embodiment 3

Adding 2-[[4-(4-acetyl-1-piperazinyl)-2-methoxyphenyl]amino]-5-(trifluoromethyl)-pyrimidin-4-one (IV) (2.06 g, 5 mmol) and phosphorus oxychloride (7.5 mL) into a reaction flask, starting stirring, cooling to 0° C. or below, and dropwisely adding 3.5 mL of 2,6-dimethylpyridine. Slowly heating to 50-70° C., and stirring to react for 9 hours while maintaining the temperature. Reducing the pressure to recover the phosphorus oxychloride, cooling the residue to room temperature, and quenching the reaction with ice water. Extracting with dichloromethane for 3 times, combining organic phases, washing with water, drying with anhydrous sodium sulfate, reducing the pressure to recover the solvent, dissolving an obtained oily matter 2-[[4-(4-acetyl-1-piperazinyl)-2-methoxyphenyl]amino]-5-(trifluoromethyl)-4-chloro-pyrimidine (V) with 25 mL of N,N-dimethylformamide, transferring into the reaction flask, and adding N-(3-aminophenyl)-2-acrylamide (1.0 g, 6 mmol) and a catalyst cesium carbonate (0.3 g). Stirring to react for 12 hours while maintaining the temperature at 90-110° C., and performing TLC detection until the reaction is finished. Filtering, concentrating under reduced pressure, adding ethyl acetate and water into the residue, and regulating pH to 5-6 with dilute acid. Separating out the organic phases, and extracting a water phase with ethyl acetate for 3 times. Combining the organic phases, washing the organic phases sequentially with pure water and brine, drying, performing reduced pressure distillation to recover the solvent, and washing with ethanol to obtain 2.15 g of an off-white solid rociletinib, wherein the yield is 77.5%. Mass spec (EI): EI-MS m/z: 556 [M+H]$^+$, $^1$H NMR (DMSO-d$_6$): δ 2.05 (s, 3H), 3.01 (m, 4H), 3.55 (m, 4H), 3.77 (m, 3H), 5.78 (d, 1H), 6.25 (d, 2H), 6.44 (m, 1H), 6.61 (s, 1H), 7.17 (s, 1H), 7.28 (m, 1H), 7.52 (m, 2H), 7.76 (s, 1H), 8.08 (s, 1H), 8.28 (s, 1H), 8.63 (s, 1H), 10.21 (s, 1H).

Embodiment 4

Adding 2-[[4-(4-acetyl-1-piperazinyl)-2-methoxyphenyl]amino]-5-(trifluoromethyl)-pyrimidin-4-one (IV) (2.06 g, 5 mmol), phosphorus tribromide (2.7 g, 10 mmol) and dichloromethane (50 mL) into a reaction flask, starting stirring, cooling to 0° C. or below, and dropwisely adding 3.0 mL of diisopropylethylamine. Slowly heating for reflux, and stirring to react for 8 hours while maintaining the temperature. After cooling to room temperature, quenching the reaction with ice water. Extracting with dichloromethane for 2 times, combining organic phases, washing with water, drying with anhydrous sodium sulfate, reducing the pressure to recover the solvent, dissolving an obtained oily matter 2-[[4-(4-acetyl-1-piperazinyl)-2-methoxyphenyl]amino]-5-(trifluoromethyl)-4-bromo-pyrimidine (V) with 25 mL of dimethyl sulfoxide, transferring into the reaction flask, and adding N-(3-aminophenyl)-2-acrylamide (1.0 g, 6 mmol) and a catalyst potassium tert-butoxide (0.5 g). Stirring to react for 12 hours while maintaining the temperature at 90-110° C., and performing TLC detection until the reaction is finished.

Filtering, concentrating under reduced pressure, adding ethyl acetate and water into the residue, and regulating pH to 5-6 with dilute acid. Separating out the organic phases, and extracting a water phase with ethyl acetate for 3 times. Combining the organic phases, washing the organic phases sequentially with pure water and brine, drying, performing reduced pressure distillation to recover the solvent, and washing with ethanol to obtain 1.98 g of an off-white solid rociletinib, wherein the yield is 71.4%. Mass spec (EI): EI-MS m/z: 556 [M+H]$^+$, $^1$H NMR (DMSO-d$_6$): δ 2.05 (s, 3H), 3.01 (m, 4H), 3.55 (m, 4H), 3.77 (m, 3H), 5.78 (d, 1H), 6.25 (d, 2H), 6.44 (m, 1H), 6.61 (s, 1H), 7.17 (s, 1H), 7.28 (m, 1H), 7.52 (m, 2H), 7.76 (s, 1H), 8.08 (s, 1H), 8.28 (s, 1H), 8.63 (s, 1H), 10.21 (s, 1H).

It should be noted that the foregoing embodiments are merely to illustrate the technical concept and features of the present invention so as to enable those skilled in the art to understand the contents of the present invention and implement the present invention accordingly, but are not intended to limit the protection scope of the present invention. All equivalent variations or modifications made according to the spirit of the present invention shall fall within the protection scope of the present invention.

What is claimed is:

1. A preparation method of rociletinib,

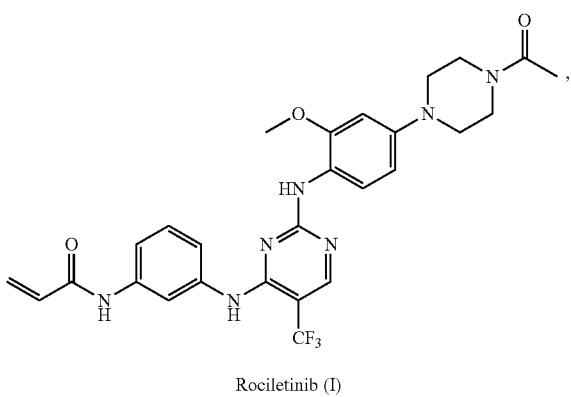 [SMILES: C=CC(=O)Nc1cccc(Nc2nc(Nc3ccc(N4CCN(C(C)=O)CC4)cc3OC)ncc2C(F)(F)F)c1]

Rociletinib (I)

characterized by comprising the following steps: performing a condensation reaction on 5-(trifluoromethyl)uracil and 4-(4-acetylpiperazin-1-yl)-2-methoxyaniline under the actions of a condensing agent and an alkali accelerator to obtain 2-[[4-(4-acetyl-1-piperazinyl)-2-methoxyphenyl]amino]-5-(trifluoromethyl)-pyrimidin-4-one, performing a halogenation reaction on the 2-[[4-(4-acetyl-1-piperazinyl)-2-methoxyphenyl]amino]-5-(trifluoromethyl)-pyrimidin-4-one and a halogenating agent under the action of an acid binding agent to obtain 2-[[4-(4-acetyl-1-piperazinyl)-2-methoxyphenyl]amino]-5-(trifluoromethyl)-4-halogeno-pyrimidine, and performing an amination reaction on the 2-[[4-(4-acetyl-1-piperazinyl)-2-methoxyphenyl]amino]-5-(trifluoromethyl)-4-halogeno-pyrimidine and N-(3-aminophenyl)-2-acrylamide under the action of a catalyst to obtain rociletinib, wherein the halogen in the 2-[[4-(4-acetyl-1-piperazinyl)-2-methoxyphenyl]amino]-5-(trifluoromethyl)-4-halogeno-pyrimidine is chlorine or bromine.

2. The preparation method of rociletinib of claim 1, characterized in that the mole ratio of 5-(trifluoromethyl)uracil to 4-(4-acetylpiperazin-1-yl)-2-methoxyaniline serving as condensation reaction raw materials is 1 to (0.5-1.5).

3. The preparation method of rociletinib of claim 1, characterized in that the condensing agent of the condensation reaction is N,N-dicyclohexylcarbodiimide, carbonyl diimidazole, N,N'-diisopropylcarbodiimide, 1-hydroxybenzotriazole, O-(benzotriazol-1-yl)-N,N,N',N'-tetramethyluronium tetrafluoroborate, O-(7-azabenzotriazol-1-yl)-N,N,N',N'-tetramethyluronium hexafluorophosphate, O-(benzotriazol-1-yl)-N,N,N',N'-tetramethyluronium hexafluorophosphate or (benzotriazol-1-yloxy)tris(dimethylamino)phosphonium hexafluorophosphate.

4. The preparation method of rociletinib of claim 1, characterized in that the alkali accelerator of the condensation reaction is triethylamine, pyridine, 2,6-dimethylpyridine, 4-dimethylaminopyridine, N-methylmorpholine, N-ethylmorpholine, diisopropylethylamine, 1,5-diazabicyclo[4.3.0]non-5-ene, 1,8-diazabicyclo[5.4.0]undec-7-ene or 1,4-diazabicyclo[2.2.2]octane.

5. The preparation method of rociletinib of claim 1, characterized in that a solvent of the condensation reaction is methylbenzene, dimethylbenzene, ethyl acetate, isopropyl acetate, butyl acetate, chloroform, dimethyl sulfoxide, N,N-dimethylformamide or acetonitrile; and the temperature of the condensation reaction is 0-120° C.

6. The preparation method of rociletinib of claim 1, characterized in that the halogenating agent of the halogenation reaction is oxalyl chloride, sulfulyl chloride, phosphorus trichloride, phosphorus pentachloride, thionyl chloride, phosphorus oxychloride or phosphorus tribromide.

7. The preparation method of rociletinib of claim 1, characterized in that the acid-binding agent of the halogenation reaction is triethylamine, pyridine, 2,6-dimethylpyridine, 4-dimethylaminopyridine, N-methylmorpholine, N-ethylmorpholine or diisopropylethylamine.

8. The preparation method of rociletinib of claim 1, characterized in that the catalyst of the amination reaction is potassium carbonate, lithium carbonate, cesium carbonate, potassium tert-butoxide, sodium tert-butoxide, sodium hydroxide, potassium hydroxide, sodium methoxide or sodium ethylate.

9. The preparation method of rociletinib of claim 1, characterized in that a solvent of the amination reaction is 1,2-dichloroethane, tetrahydrofuran, acetonitrile, dioxane, benzene, methylbenzene, dimethylbenzene, dimethyl sulfoxide or N,N-dimethylformamide.

10. The preparation method of rociletinib of claim 1, characterized in that the temperature of the amination reaction is 25-150° C.

* * * * *